United States Patent [19]
Allen et al.

[11] Patent Number: 5,224,490
[45] Date of Patent: Jul. 6, 1993

[54] DISPOSABLE TOCODYNAMOMETER WITH SELF-ADJUSTING BELLOWS

[75] Inventors: George R. Allen, Grand Island; David M. DiSabito, Clarence; Goran Enhorning, Buffalo, all of N.Y.

[73] Assignee: Graphic Controls Corporation, Buffalo, N.Y.

[21] Appl. No.: 771,724

[22] Filed: Oct. 4, 1991

[51] Int. Cl.⁵ .................................................. A61B 5/103
[52] U.S. Cl. ...................................... 128/775; 128/778; 73/862.581
[58] Field of Search ............... 128/782, 778, 775, 774, 128/748, 721, 722; 73/862.581, 862.582, 729

[56] References Cited

U.S. PATENT DOCUMENTS

| | | | |
|---|---|---|---|
| Re. 31,158 | 2/1983 | Carter et al. | 364/415 |
| 1,637,829 | 8/1927 | Lurie | 128/802 |
| 2,194,809 | 3/1940 | Powell, Jr. | 128/721 |
| 2,233,506 | 3/1941 | Azaretti | 128/721 |
| 3,520,294 | 7/1970 | Fuzzell et al. | 128/775 |
| 3,599,628 | 8/1971 | Abbenante | 128/698 |
| 3,662,743 | 5/1972 | Amarante et al. | 128/748 |
| 3,726,273 | 4/1973 | Cole | 128/778 |
| 3,752,148 | 8/1973 | Schmalzbach | 128/686 |
| 3,913,563 | 10/1975 | Ball | 128/775 |
| 3,945,373 | 3/1976 | Tweed et al. | 128/782 |
| 4,055,839 | 10/1977 | Skeggs | 340/279 |
| 4,114,188 | 9/1978 | Carter et al. | 364/415 |
| 4,122,837 | 10/1978 | Leonard | 128/774 |
| 4,175,562 | 11/1979 | Honan | 606/202 |
| 4,210,154 | 7/1980 | Klein | 128/685 |
| 4,240,444 | 12/1980 | Virgulto et al. | 128/782 |
| 4,325,387 | 4/1982 | Helfer | 128/748 |
| 4,399,809 | 8/1983 | Baro et al. | 600/31 |
| 4,413,620 | 11/1983 | Tucker | 128/869 |
| 4,592,342 | 6/1986 | Salmasian | 128/898 |
| 4,622,957 | 11/1986 | Curlee | 602/13 |
| 4,640,295 | 2/1987 | Isaacson | 128/748 |
| 4,696,307 | 9/1987 | Montgieux | 128/721 |
| 4,747,415 | 5/1988 | Lavoisier | 128/774 |
| 4,813,428 | 3/1989 | Muraki et al. | 128/721 |
| 4,895,162 | 1/1990 | Dolliver | 128/721 |
| 4,989,615 | 2/1991 | Hochberg | 128/774 |
| 5,022,402 | 6/1991 | Schieberl et al. | 128/671 |
| 5,070,888 | 12/1991 | Hon et al. | 128/778 |

FOREIGN PATENT DOCUMENTS 230768  12/1985  Fed. Rep. of Germany.

OTHER PUBLICATIONS

Parsley, Quentin, "The Act Disposable Tocotonometer" International Biomedics, Inc. Brochure Sep. 1988 pp. 1–3.

LaCroix, George E. "Monitoring Labor by an External Tokodynamometer", American Journal of Obstetrics & Gynec. May 1, 1968 pp. 111–119.

Smyth, C. N. et al "The Guard-Ring Tocodynamometer" Journal of Obstetrics and Gynaecology, 64:59–66, 1957.

*Primary Examiner*—Max Hindenburg
*Assistant Examiner*—Guy V. Tucker
*Attorney, Agent, or Firm*—Ratner & Prestia

[57] ABSTRACT

A non-invasive, disposable, self-adjusting tocodynamometer (10) for monitoring uterine contractions of a patient during pregnancy, labor, and delivery The tocodynamometer includes a pressure-sensitive, fluid, filled bellows (20) responsive to changes in the hardness of the uterus during contractions The bellows has one face which projects into the patient's soft tissue in the abdomen and adjacent the uterus, rending the tocodynamometer sensitive even for obese patients. A plate (22) supports the bellows and provides structure for attaching the tocodynamometer to the patient. A wall (30) formed on the plate receives the bellows as it is compressed during use. A conduit (14) connects the bellows to a pressure transducer (12) which, in turn, is connected to a monitor (16). The bellows, conduit, and pressure transducer form a closed system containing the working fluid.

33 Claims, 1 Drawing Sheet

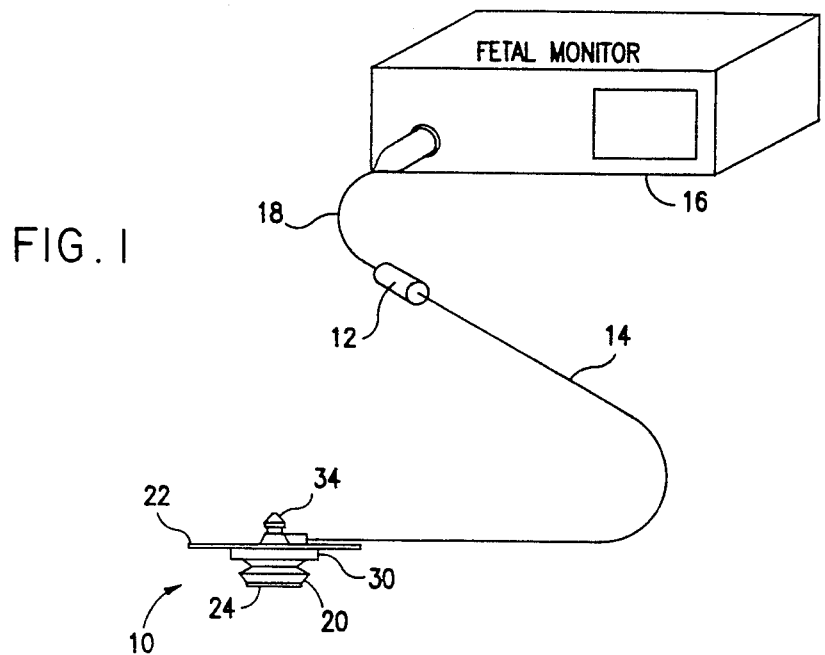
FIG. 1
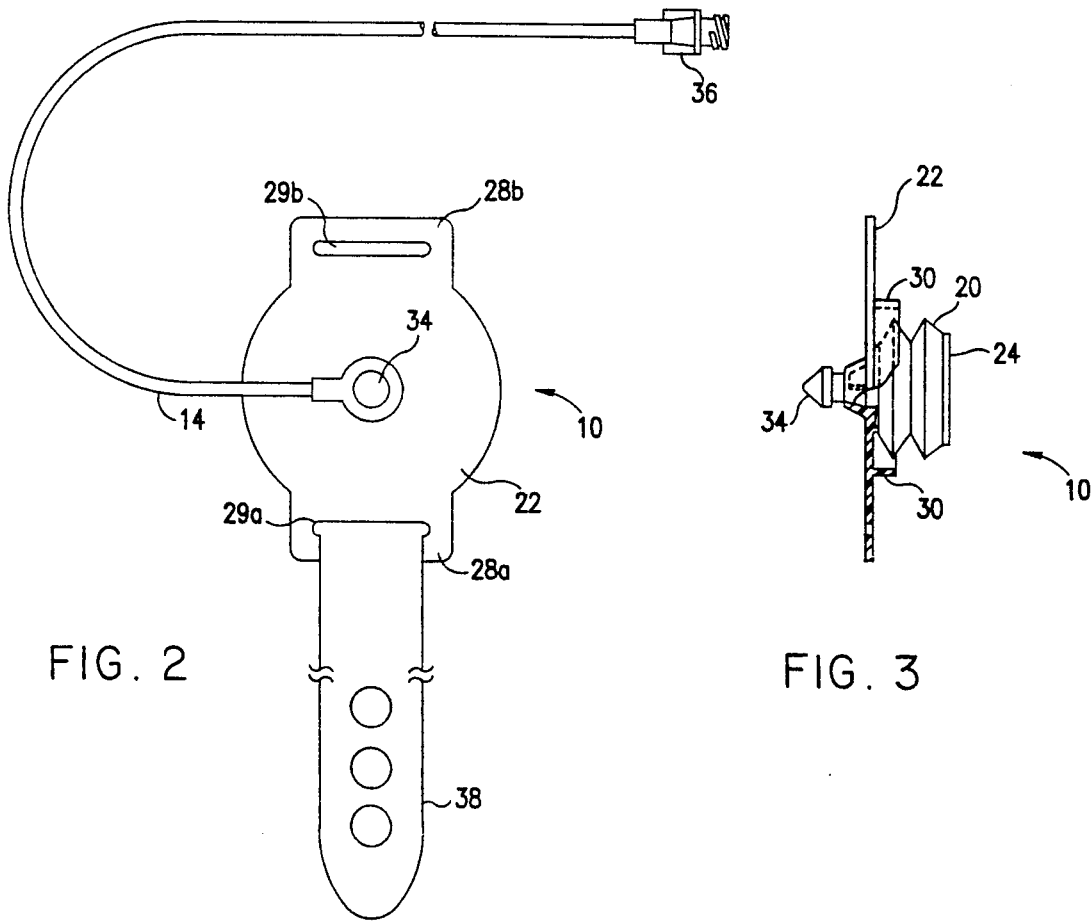
FIG. 2
FIG. 3

DISPOSABLE TOCODYNAMOMETER WITH SELF-ADJUSTING BELLOWS

BACKGROUND OF THE INVENTION

The present invention relates generally to fetal monitoring devices and, more particularly, to a disposable, non-invasive, self-adjusting tocodynamometer used to monitor uterine activity during labor.

The procedure of monitoring and analyzing uterine contractions, during both pregnancy and labor, yields significant information concerning the condition of the fetus as well as the advancement of labor. Such a procedure is useful both during routine pregnancies and especially during difficult pregnancies, those which have increased risk to the health of the fetus, to systematically evaluate fetal stress. Information indicating fetal distress during pregnancy, labor, and delivery will prompt remedial action, including caesarean delivery, which may save the fetus from harm and even death. Thus, contraction frequency, duration, intensity, and resting tone are now monitored as part of accepted, standard, obstetrical procedure.

The fetal monitors widely used to monitor the uterine activity of pregnant women, as well as the condition of the fetus while in the uterus, are typically quite sophisticated. Examples of currently available fetal monitors include the FetaScan from International Biomedics, Inc.; the Corometrics 115; and the Hewlett-Packard 8040A. Regardless of their sophistication, however, fetal monitors require a device or element to actually sense the uterine contractions. In a contraction, the abdomen hardens, and the shape of the abdomen changes, in part because the muscles in the anterior ligament of the uterus pull it forward during the contraction.

One example of such a sensing element is a catheter which is capable of measuring uterine activity within a uterine cavity itself. U.S. Pat. No. 3,599,628 issued to Abbenante et al. is an example of such a sensing element. Such devices are invasive and position sensitive; they must be positioned adjacent to the fetus for good results. Thus, movement of the fetus will often affect the results adversely.

Other devices can sense uterine activity externally and non-invasively. The advantages offered by those devices, known as tocodynamometers, have caused them to be widely used with fetal monitors. Tocodynamometers measure the hardness of the abdominal wall, which is an indication of uterine activity, through various mechanical elements. The tocodynamometer is held adjacent to the patient's abdomen, usually by a belt-like device, in the vicinity of the fundus (the top of the uterus). The tocodynamometer is initialized by setting the recording level so that it is near zero between contractions. The output of the device is transmitted to the fetal monitor through a pressure transducer, the transducer converting the pressure change information received from the tocodynamometer to an electrical signal which it delivers to the fetal monitor.

Existing tocodynamometers require frequent adjustment as the fetus moves in the uterus. Such adjustment and the weight of the devices cause discomfort for the patient. Tocodynamometers now in use also have other disadvantages, including their high cost, their fragile structures, and the difficulty and expense of cleaning and repairing them after use.

An example of another assembly for monitoring uterine activity is disclosed in U.S. Pat. No. 4,989,615 issued to Hochberg. The Hochberg assembly uses a relatively flat bladder-element, coupled with a resilient insert. The bladder and insert combination render the assembly less effective, if not inoperative, on patients having substantial amounts of soft tissue in the abdominal area. The excess soft tissue between the uterine muscle and the bladder and insert interferes with the assembly's sensitivity to contractions. Thus, the Hochberg assembly is not effectively functional for all patients—and may especially experience problems when used on obese patients.

U.S. Pat. No. 3,945,373, issued to Tweed et al., discloses an example of a tocodynamometer which has an adjustable, patient-contacting member potentially effective for use with obese patients. The disclosed device has a threaded shaft with the patient. contacting member disposed at one end of the shaft. The shaft can be adjusted up or down like a screw. Although adjustable, the tocodynamometer has several practical drawbacks, including: (1) the cost of manufacturing the complicated, electro-mechanical device, and (2) the risk of patient discomfort as the shaft impinges the abdomen.

To overcome the shortcomings of the existing devices for sensing uterine activity and transmitting information to a fetal monitor, a new, external, non-invasive tocodynamometer is provided. The general object of the present invention is to minimize the manufacturing costs of the assembly while meeting the patient's needs. By reducing manufacturing costs, the tocodynamometer becomes disposable. A related object is to provide a disposable device, therefore, which eliminates the cost and time required to clean and repair non-disposable devices. Another specific object is to assure a continually functional device, especially for obese patients, by providing increased sensitivity. Still another object is to increase patient comfort by reducing both the weight of the tocodynamometer and the number of adjustments necessary to assure optimum performance.

SUMMARY OF THE INVENTION

To achieve these and other objects, and in view of its purpose, the present invention provides a disposable tocodynamometer which includes a fluid-filled, self-adjusting bellows sealed to a back plate for support during use. The plate provides structure for attaching the tocodynamometer to a patient and is able to engage an adjustable belt, strap, or the like. A wall on the plate receives the bellows as it is compressed during use, defining the minimum height of the bellows when fully compressed. Also included in the tocodynamometer is a conduit for conveying pressure changes within the bellows to a pressure transducer. The pressure transducer is, in turn, connected to a fetal monitor.

It is to be understood that both the foregoing general description and the following detailed description are exemplary, but not restrictive, of the invention.

BRIEF DESCRIPTION OF THE DRAWINGS

The invention is best understood from the following detailed description when read in connection with the accompanying drawings, in which:

FIG. 1 is a perspective view of a disposable tocodynamometer constructed in accordance with the principles of the present invention illustrating the assembly attached to a pressure transducer and, in turn, to a fetal monitor;

FIG. 2 is a top view of the disposable tocodynamometer of the present invention; and FIG. 3 is a side view and partial cross section of the disposable tocodynamometer shown in FIG. 2.

DETAILED DESCRIPTION OF THE INVENTION

Like reference numerals have been used throughout the various figures of the drawing to identify like elements. Shown in FIG. 1 is a tocodynamometer 10 constructed in accordance with the present invention. Tocodynamometer 10 is connected to a pressure transducer 12 via a conduit 14. Pressure transducer 12 is connected, in turn, to a fetal monitoring device 16 via a cable 18.

As shown in FIGS. 1 and 3, tocodynamometer 10 includes a fluid-filled bellows 20. Bellows 20 is sealed against a back plate 22 on one end and has a foam pad 24 on its opposite end for contacting the patient in a comfortable manner.

Bellows 20 may be of any suitable shape. In the preferred embodiment, however, bellows 20 has a deep, cylindrical shape which can project into soft tissue, especially that of an obese patient, without performance loss or patient discomfort. The height of bellows 20 is self-adjusting (on the order of 1 inch) according to the amount of soft tissue on the patient—yet the force generated by a contraction of a particular strength creates a constant pressure reaction in the bellows.

Plate 22 may also be of any suitable shape. In the preferred embodiment, however, as shown in FIG. 2, plate 22 is circular with a pair of tabs 28a and 28b extending from opposite sides. A suitable diameter for the circular portion of plate 22 is about 2.75 inches; a suitable dimension for the length defined by tabs 28a and 28b is about 3.5 inches. Tabs 28a and 28b have slots 29a and 29b, respectively, for attachment to an adjustable belt 38.

Alternatively or in combination, a projection or button 34 is provided on the face of plate 22 opposite bellows 20 for engaging one or more of a series of holes in an adjustable belt 38. A suitable height for tocodynamometer 10 from the bottom of foam pad 24, which contacts the patient, to the top of button 34 is about 1.5 inches. A self-adhesive strap is also suitable for attaching tocodynamometer 10 to a patient.

Plate 22 is constructed of molded, rigid plastic for supporting bellows 20 when bellows 20 is expanded or compressed during use. As is known to those skilled in the art, plate 22 can be constructed of most any rigid and relatively inexpensive material suitable for the present invention. Button 34 may be integrally molded as part of plate 22.

As shown in FIG. 3, surrounding bellows 20 and attached to plate 22 is a wall 30. In the preferred embodiment, wall 30 is circular in shape to compliment the shape of bellows 20 by outlining the perimeter of bellows 20. Preferably, wall 30 is constructed of the same material as plate 22; wall 30 may be integrally formed with plate 22 as, for example, by molding plate 22 and wall 30 together from plastic. As known by those skilled in the art, however, most any rigid and relatively inexpensive material would be suitable to construct wall 30. Because wall 30 is rigid, the height of wall 30 sets the minimum height permissible for bellows 20 when fully compressed.

As shown in FIGS. 1 and 2, attached to plate 22 on its face opposite bellows 20 is a hollow, plastic conduit or pressure line 14. Conduit 14 penetrates inside bellows 20 on one end. On its opposite end, conduit 14 has a fitting 36 for connection with reusable pressure transducer 12 and, in turn, with fetal monitor 16. Fitting 36, in the preferred embodiment, is a female Luer fitting constructed of molded plastic.

Tocodynamometer 10 may be used in the following manner. First, tocodynamometer 10 is attached to the patient's abdomen in the vicinity of the uterus using an adjustable belt 38, self-adhesive strip, or other equivalent securing means. Foam pad 24 contacts the patient once tocodynamometer 10 is secured.

Depending on the amount of soft tissue at and around the placement of tocodynamometer 10, the height of bellows 20 adjusts itself as a function of the resisting force of the contacted surface area. Specifically, the presence of substantial amounts of soft tissue (fat), which will exert less resisting force than hard tissue (muscle), will allow bellows 20 to expand and increase in height. This self-adjusting feature allows tocodynamometer 10 to function equally well independent of the amount of soft tissue in the patient's abdomen.

After tocodynamometer 10 has been secured and the initial pressure settings for bellows 20 calibrated as a function of abdominal inactivity between contractions, the invention operates as a closed system in which he working fluid (typically air) within bellows 20 functions to transmit pressure change information generated within bellows 20 by uterine contractions to pressure transducer 12 via conduit 14 and, in turn, to fetal monitor 16 via cable 18.

It should be readily apparent that tocodynamometer 10 can be made relatively inexpensively. Consequently, tocodynamometer 10 can be used once and discarded; it is disposable.

Although the invention is illustrated and described herein as embodied in a disposable tocodynamometer including a bellows, which on one end is sealed to a plate attached to a patient and on the other end has a foam pad, and a fluid conduit for conveying pressure change information from the bellows to a pressure transducer, the invention is nevertheless not intended to be limited to the details shown. Rather, various modifications may be made in the details within the scope and range of equivalence of the claims and without departing from the spirit of the invention.

What is claimed:

1. A non-invasive, disposable tocodynamometer for monitoring uterine contractions of a patient during pregnancy, labor, and delivery, said tocodynamometer comprising:

a pressure-sensitive, fluid-filled bellows having one face adapted to project into said patient's sort tissue in a position on the abdomen and adjacent the uterus and an accordion-like wall defining a height self-adjusting according to the amount of said patient's soft tissue, said bellows responsive to changes in the hardness of the uterus during contractions and compressing during increased hardness of the uterus;

means for securing said bellows to the abdomen of said patient;

means for monitoring fluid pressure changes within said bellows caused by hardness changes in the uterus during contractions; and a conduit connecting said bellows to said fluid pressure monitoring means, whereby said bellows, said conduit, and said fluid pressure monitoring means form a closed system containing said fluid.

2. A tocodynamometer as claimed in claim 1 wherein said fluid is air.

3. A tocodynamometer as claimed in claim 1 wherein said bellows has a perimeter defining a cylindrical shape.

4. A tocodynamometer as claimed in claim 1 wherein said fluid pressure monitoring means is a pressure transducer.

5. A tocodynamometer as claimed in claim 1 wherein said conduit is a hollow, plastic pressure line which penetrates inside said bellows on one end and engages said fluid pressure monitoring means on its opposite end.

6. A tocodynamometer as claimed in claim 5 wherein said conduit has a female Luer fitting on said opposite end for engaging said fluid pressure monitoring means.

7. A tocodynamometer as claimed in claim 1 further comprising a rigid plate having a bottom to which said bellows is sealingly attached and a top, said plate supporting said bellows during use.

8. A tocodynamometer as claimed in claim 7 wherein said securing means includes a button disposed on said top of said plate and an adjustable belt having holes for engaging said button.

9. A tocodynamometer as claimed in claim 7 wherein said securing means includes slots formed in said plate and an adjustable belt for engaging said slots.

10. A tocodynamometer as claimed in claim 7 wherein said plate has a rigid wall formed on said bottom of said plate for surrounding and receiving said bellows as said bellows is compressed during use, said wall defining the minimum height achieved by said bellows when fully compressed.

11. A tocodynamometer as claimed in claim 7 wherein said plate is plastic.

12. A tocodynamometer as claimed in claim 10 wherein said wall is integrally formed with said plate.

13. A tocodynamometer as claimed in claim 1 wherein said projecting face of said bellows has a foam pad to assure patient comfort.

14. A non-invasive, disposable tocodynamometer for monitoring uterine contractions of a patient during pregnancy, labor, and delivery, said tocodynamometer comprising:
- a pressure-sensitive, fluid-filled bellows having one face adapted to project into said patient's soft tissue in a position on the abdomen and adjacent the uterus and an accordion-like wall defining a height self-adjusting according to the amount of said patient's soft tissue, said bellows responsive to changes in the hardness of the uterus during contractions and compressing during increased hardness of the uterus;
- a foam pad affixed to said projecting face of said bellows to assure patient comfort;
- a rigid plate having a bottom to which said bellows is sealingly attached and a top, said plate supporting said bellows during use;
- means for securing said bellows to the abdomen of said patient;
- a pressure transducer for monitoring changes within said bellows caused by hardness changes in the uterus during contractions; and
- a conduit which penetrates inside said bellows on one end and engages said pressure transducer on its opposite end to connect said bellows to said pressure transducer, whereby said bellows, said conduit, and said pressure transducer form a closed system containing said fluid.

15. A tocodynamometer as claimed in claim 14 wherein said fluid is air.

16. A tocodynamometer as claimed in claim 14 wherein said bellows has a perimeter defining a cylindrical shape.

17. A tocodynamometer as claimed in claim 14 wherein said conduit is a hollow, plastic pressure line.

18. A tocodynamometer as claimed in claim 17 wherein said conduit has a female Luer fitting on said opposite end for engaging said pressure transducer.

19. A tocodynamometer as claimed in claim 14 wherein said securing means includes a button disposed on said top of said plate and an adjustable belt having holes for engaging said button.

20. A tocodynamometer as claimed in claim 14 wherein said securing means includes slots formed in said plate and an adjustable belt for engaging said slots.

21. A tocodynamometer as claimed in claim 14 wherein said plate has a rigid wall formed on said bottom of said plate for surrounding and receiving said bellows as said bellows is compressed during use, said wall defining the minimum height achieved by said bellows when fully compressed.

22. A tocodynamometer as claimed in claim 14 wherein said plate is plastic.

23. A tocodynamometer as claimed in claim 21 wherein said wall is integrally formed with said plate.

24. In a fetal monitoring system used to monitor uterine contractions of a pregnant women having a pressure sensitive element for sensing uterine contractions; a pressure transducer for measuring the pressure in said pressure-sensitive element and converting pressure changes into an electrical signal; a monitor for receiving, analyzing, and displaying said electrical signal; and a cable for transmitting said electrical signal from said transducer to said monitor; wherein the improvement comprises a pressure-sensitive element including:
- a fluid-filled bellows having one face adapted to project into said patient's soft tissue in a position on the abdomen an d adjacent the uterus and an accordion-like wall defining a height self-adjusting according to the amount of said patient's soft tissue, said bellows responsive to changes in the hardness of the uterus during contractions and compressing during increased hardness of the uterus;
- a foam pad affixed to said projecting face of said bellows to assure said women's comfort;
- a rigid plate having a bottom to which said bellows is sealingly attached and a top, said plate supporting said bellows during use;
- means for securing said bellows to the abdomen of said woman; and
- a conduit which penetrates inside said bellows on one end and engages said pressure transducer on its opposite end to connect said bellows to said pressure transducer, whereby said bellows, said conduit, and said pressure transducer form a closed system containing said fluid.

25. A fetal monitoring system as claimed in claim 24 wherein said fluid is air.

26. A fetal monitoring system as claimed in claim 24 wherein said bellows has a perimeter defining a cylindrical shape.

27. A fetal monitoring system as claimed in claim 24 wherein said conduit is a hollow, plastic pressure line.

28. A fetal monitoring system as claimed in claim 27 wherein said conduit has a female Luer fitting on said opposite end for engaging said pressure transducer.

29. A fetal monitoring system as claimed in claim 24 wherein said securing means includes a button disposed on said top of said plate and an adjustable belt having holes for engaging said button.

30. A fetal monitoring system as claimed in claim 24 wherein said securing means includes slots formed in said plate and an adjustable belt for engaging said slots.

31. A fetal monitoring system as claimed in claim 24 wherein said plate has a rigid wall formed on said bottom of said plate for surrounding and receiving said bellows as said bellows is compressed during use, said wall defining the minimum height achieved by said bellows when fully compressed.

32. A fetal monitoring system as claimed in claim 24 wherein said plate is plastic.

33. A fetal monitoring system as claimed in claim 31 wherein said wall is integrally formed with said plate.

* * * * *